United States Patent
Carnahan

(10) Patent No.: US 6,363,801 B1
(45) Date of Patent: Apr. 2, 2002

(54) APPARATUS AND PROCESS FOR SELECTING AND POSITIONING PARTICLES

(75) Inventor: James Claude Carnahan, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/558,782

(22) Filed: Apr. 26, 2000

(51) Int. Cl.[7] .............................. B01L 3/02; G01N 1/00; G01N 1/14
(52) U.S. Cl. .................. 73/864.11; 73/864; 73/864.21; 73/864.35
(58) Field of Search ........................ 73/863.21, 863.23, 73/863.24, 864.34, 864.73, 865.5, 864.11, 864.21, 864.35, 28.01; 436/177

(56) References Cited

U.S. PATENT DOCUMENTS

| | | | |
|---|---|---|---|
| 2,656,508 A | * 10/1953 | Coulter | 324/439 |
| 3,380,584 A | * 4/1968 | Fulwyler | 73/865.5 |
| 3,932,141 A | 1/1976 | Beall et al. | |
| 4,299,795 A | 11/1981 | Bates | |
| 5,382,512 A | 1/1995 | Smethers et al. | |
| 5,919,356 A | * 7/1999 | Hood | 73/836.23 |
| 5,935,859 A | 8/1999 | Elliott et al. | |
| 5,979,251 A | 11/1999 | James et al. | |
| 6,076,410 A | * 6/2000 | Renslow | 73/864.34 |

FOREIGN PATENT DOCUMENTS

| | | |
|---|---|---|
| DE | 2050885 | 4/1971 |
| WO | 17383 | 4/1998 |
| WO | 58476 | 11/1999 |

OTHER PUBLICATIONS

International Search Report.

* cited by examiner

Primary Examiner—Hezron Williams
Assistant Examiner—Katina Wilson
(74) Attorney, Agent, or Firm—S. Bruce Brown; Noreen C. Johnson

(57) ABSTRACT

An embodiment of the apparatus comprises a hollow tubular body (a) of a cross-section size larger than the diameter of any single particle but smaller than twice the diameter to accommodate passage of a single particle at a time through the hollow tubular body and (b) of a length to accommodate a predetermined number of particles. The apparatus includes an obstruction within the body that permits passage of fluid but prevents passage of a particle. The apparatus also includes a force applicator at one end of the tubular body to apply a force to draw a flow of fluid and particles into an end of the element to fill the hollow tubular body with particles along a length of the body up to the obstruction and to maintain the force so as to retain the particles within the body while transporting the retained particles to a location.

22 Claims, 6 Drawing Sheets

APPARATUS AND PROCESS FOR SELECTING AND POSITIONING PARTICLES

BACKGROUND OF THE INVENTION

The present invention relates to an apparatus and process for selecting and positioning particles. More particularly, the invention relates to an apparatus and process for selecting and arraying particles for a combinatorial chemistry multiple screening process.

In experimental reaction systems, each potential combination of reactants, catalysts and conditions must be evaluated in a manner that provides correlation to performance in a production scale reactor. Since about 1970, combinatorial organic synthesis (COS) has provided an important tool to address the requirements of experimental systems. COS is a systematic and repetitive synthesis that uses sets of chemical "building blocks" to form a diverse set of molecular entities. As with traditional research, COS relies on organic synthesis methodology. However instead of synthesizing a single compound, COS exploits automation and miniaturization to synthesize large libraries of compounds; a procedure that can involve successive stages, each of which produces a chemical modification of an existing molecule of a preceding stage. The synthesis produces large numbers of diverse compounds, which can be screened for various activities.

In a typical approach to COS, arrayed, spatially addressable building blocks are reacted systematically on particle supports. The particles are distributed into a two-dimensional array so that each variant in a combinatorial library can be identified by its position in the array. The array can consist of a set of plates, each having rows and columns of wells, with one particle, or some other predetermined number of particles contained in each well. The particles are typically made of polystyrene. They serve as substrates for different compounds produced in the process of split and combine synthesis. Ultimately, synthesized compounds are stripped from the particles and tested for activity. The identity of an active compound can be determined by spectrographic analysis in the light of the information available concerning the reaction histories of the particles.

Typically, the particles are arrayed in columns and rows on plates so that they are geometrically compatible with screening systems. For example 8×12 arrays or other formats such as 384- or 896-well configurations are common. The particles are spherical and of extremely small size, e.g. 300 mm in diameter. Consequently, they are difficult to handle. It is very difficult to separate a single particle from a mixture of particles. Still another problem encountered in particle arraying is that the particles tend to be fragile and are prone to crumbling when mechanically agitated. Current processes of arraying particles include manual picking and hydrodynamic sorting in which particles are allowed to flow though an aperture. Manual picking is slow and tedious. A hydrodynamic method is slow and the equipment used is prone to clogging.

There remains a long-felt, yet unsolved need for a simple, rapid and reliable process and apparatus for selecting and positioning particles, particularly combinatorial processing particles that can reliably deliver a single particle to each point in an array.

BRIEF SUMMARY OF THE INVENTION

Accordingly, the present invention provides an apparatus and process for selecting and positioning particles that meet this need. In an exemplary embodiment, the apparatus comprises a hollow tubular body (a) of a cross-section size larger than the diameter of any single particle but smaller than twice the diameter to accommodate passage of a single particle at a time through the hollow tubular body and (b) of a length to accommodate a predetermined number of particles. The apparatus includes an obstruction within the body that permits passage of fluid but prevents passage of a particle. The apparatus also includes a force applicator at one end of the tubular body to apply a force to draw a flow of fluid into the hollow tubular body with particles along a length of the body up to the obstruction and to maintain the force so as to retain the particles within the body while transporting the retained particles to a location.

In another embodiment, the invention also relates to a process for selecting particles, comprising applying a force to draw a flow of fluid with suspended particles into an end of a hollow tubular body and through the body and impeding the flow in a manner so as to permit fluid to continue to flow while retaining particles within the body at a predetermined point so as to load the body with a selection of particles.

In an alternative embodiment, the invention also relates to a process for selecting and positioning particles. According to the process, a suspension comprising a mixture of substantially uniform sized particles is established in a fluid. A hollow tubular element is introduced into the suspension. The element comprises (i) a hollow tubular body (a) of a cross-section size larger than the diameter of any single particle but smaller than twice the diameter to accommodate passage of a single particle at a time through the hollow tubular body and (b) of a length to accommodate a predetermined number of particles and (ii) an obstruction within the body that permits passage of fluid but prevents passage of a particle. A force is applied to draw a flow of fluid into an end of the element to fill the hollow tubular body with particles along a length of the body to the obstruction. The force is maintained so as to retain the particles within the body while transporting the retained particles to a location. The retained particles are deposited at the location by releasing the force.

DETAILED DESCRIPTION OF THE INVENTION

In one embodiment, the apparatus consists of a sampling tube with an inside diameter larger than the diameter of the largest particle to be transported. The length of the tube is determined so as to hold a desired number of particles. An obstruction partially blocks the bore of the tube at a determined length to permit passage of fluid but not particles. The apparatus can include a three-way valve or can be a mechanically or electrically operated syringe. The material of the tube can be polymer, ceramic, glass or metal or combinations thereof.

These and other features will become apparent from the drawings and following detailed discussion, which by way of example without limitation describes preferred embodiments of the present invention.

Figure 1:
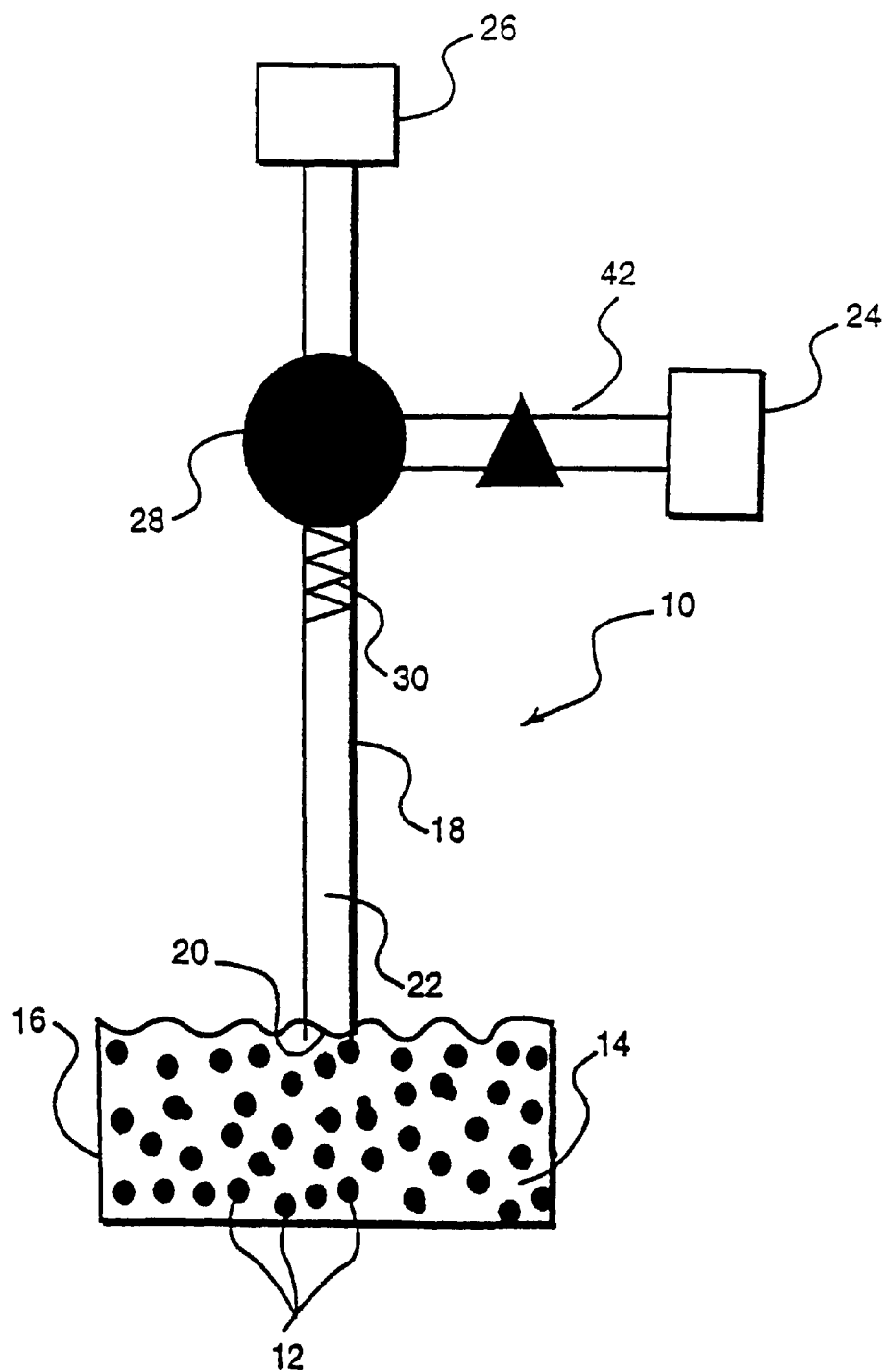
FIGS. 1 to 4 are schematic representations of embodiments of an apparatus of an embodiment of the invention.
Figure 2:
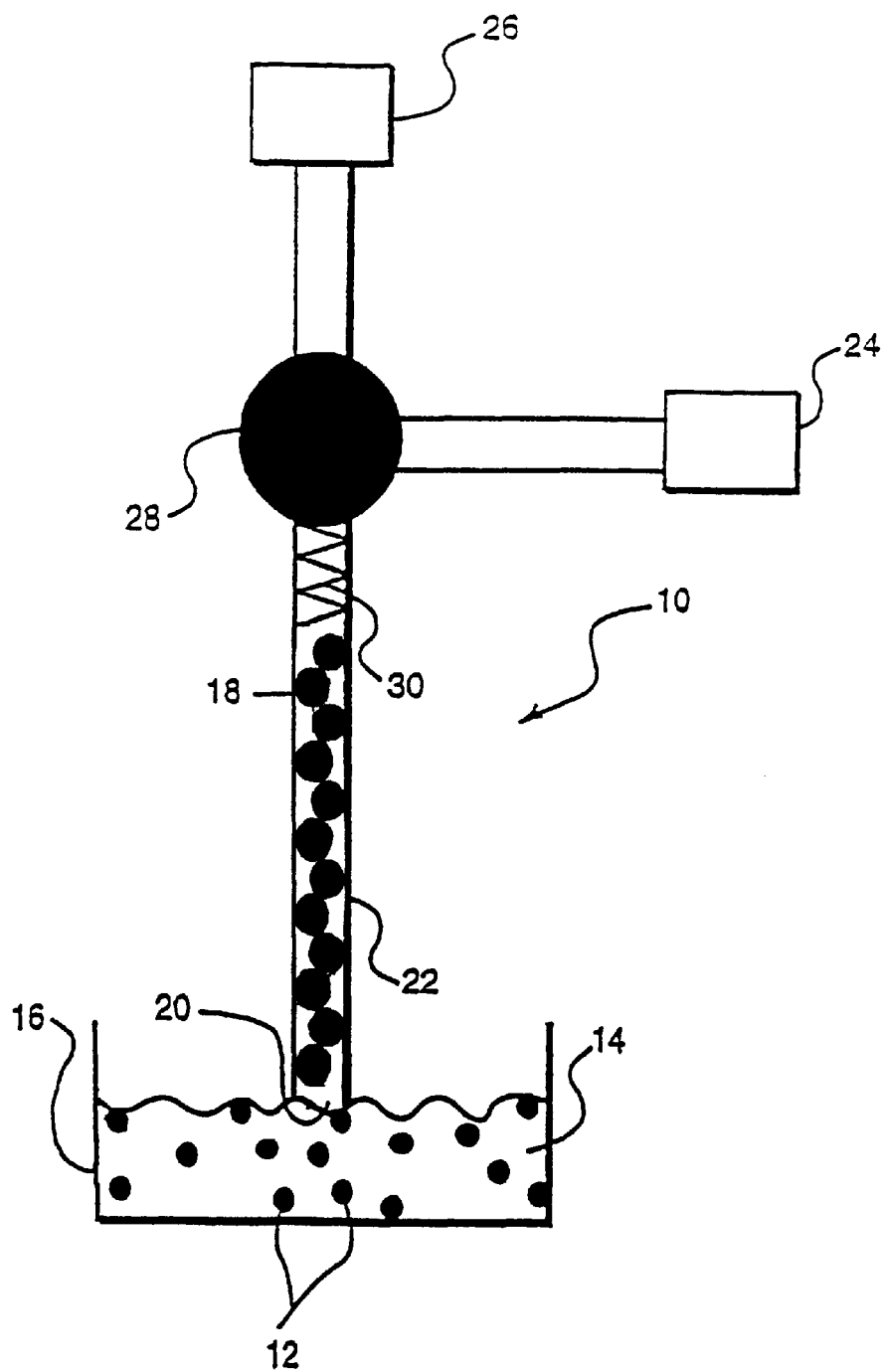

FIG. 1 and FIG. 2 schematically illustrate a preferred embodiment of the invention. Selection apparatus 10 is shown in FIG. 1 before selection and in FIG. 2 after selection of particles 12. The particles 12 are shown suspended in fluid 14 contained in container 16. Selection apparatus 10 includes hollow tubular body 18 with tip 20. The body 18 is characterized by a cross-section bore 22 size that is larger than the diameter of any single particle 12 but that is smaller than twice the diameter. The bore 22 accommodates passage of a single particle 12 at a time through the tubular body 18. The length of tubular body 18 is selected to accommodate a predetermined number of particles 12. The body 18 of the apparatus 10 is connected to a vacuum source 24, which can be a valve and pump apparatus or a syringe and diaphragm arrangement. The body 18 is also connected to a fluid source 26. For example, the body 18 can include a valved gravity fed system, a pump and vessel apparatus or a syringe arrangement. The vacuum source 24 and fluid source 26 are connected to bore 22 of the body 18 via three way valve 28, which can be activated to apply a vacuum or to apply a fluid to the body 18 within bore 22. Included within bore 22 is obstruction 30, which is any structure that impedes the passage of a particle but permits flow of fluid. Examples include a filter such as a screen, a porous metal, ceramic or glass frit, a spring or straight wire or a concentric ring shape.

In operation, tip 20 of the tubular body 18 is immersed in a stirred suspension of particles such as catalyst or COS bead particles and a vacuum is applied to the opposite end of the body by means of vacuum source 24 via valve 28. Fluid 14 and suspended particles 12 are sucked into the tube until the particles 12 encounter obstruction 30 (FIG. 2). The obstruction 30 partially blocks the tube bore 22 arresting the particles 12 but permitting advancement of fluid 14. Particles entering the tube will rest against earlier particles with a force determined by applied vacuum, passage volume of the tube, difference between the diameter of a particle and the diameter of the tube bore 22, the number of particles in the tube and viscosity of the suspending fluid.

After the tube is filled, excess particles that adhere at tip 20 can be mechanically removed by a wiper or the like. The tube containing a measured number of particles as shown in FIG. 2, then can be transported to a receiving vessel for dispensing. There, three-way valve 28 can be activated to terminate the application of vacuum and to apply fluid flow into the bore 22 from fluid source 26. The fluid flow expels particles 12 that were held in the bore 22. A robotic transport device can be used to transport the selection apparatus 10 between the suspended particle 12 source and a reaction location such as a well array of a combinatorial reaction plate.

In an alternative embodiment, the selection apparatus 10 can be used to count a number of positioned and delivered particles 12. In this embodiment, the size of the tube bore 22 relative to the particles 12 to be selected can be determined and the apparatus 10 used for high delivery precision. Preferably, the bore 22 diameter is chosen to be slightly larger than a largest particle in a particle distribution and the length is chosen to be slightly smaller than the diameter of an excess particle over a determined number of particles to be selected. This results in a roughly linear string of particles in the tube bore 22. As a tube bore 22 diameter is selected that increase relative to particle diameter, bridging of particles (stacking faults) and void formation increase and become high at a tube diameter greater than twice particle diameter. Consequently, tube bore 22 diameter to mean particle 12 diameter distribution ratio should be less than about 2:1, desirably less than about 1.5 to 1 and preferably less than about 1 to 1.

Figure 3:
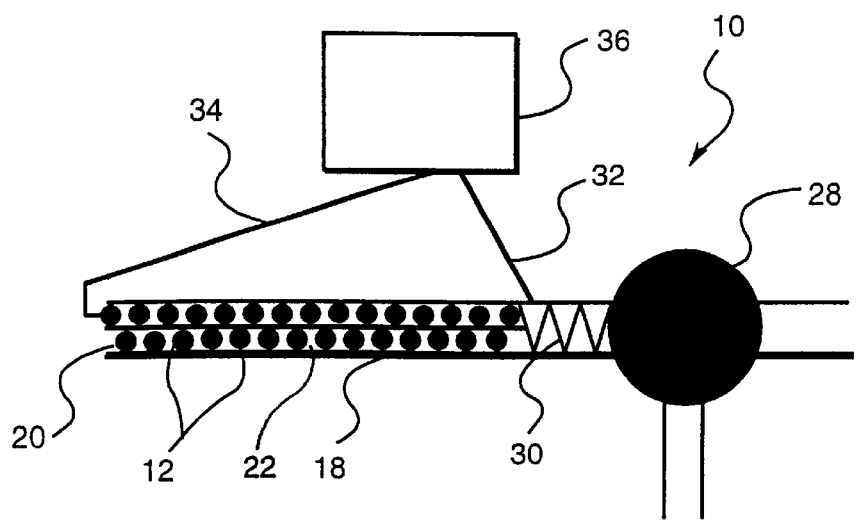
Figure 4:
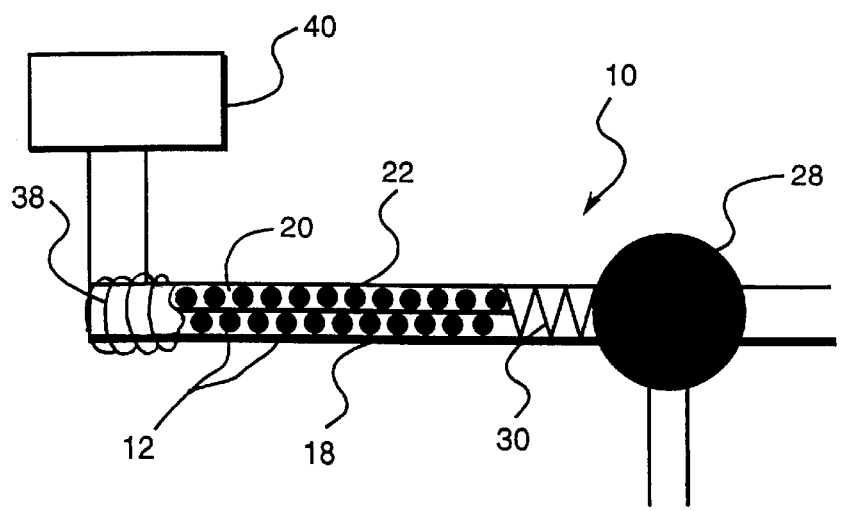

In alternative embodiments, the apparatus and process is capable of determining when the sampling tube bore 22 is filled with particles 12 in contact. FIG. 3 shows electrical leads 32, 34 applied at opposite ends near retained particles 12 within the bore 22 to sense whether the particles 12 are in continuous contact. This process works best with sampling tubes made from electrically insulating materials. In an example, a sampling tube body 18 is made of Teflon® polymer. The tube body 18 includes an obstruction 30 that has an electrical connection 32 and a tip 20 with another electrical connection 34. The electrical connections complete a circuit for electrical continuity when conductive particles are in contact in the tube bore 22. The circuit includes sensor 36. If the bore 22 is incompletely filled, air gaps cause high or infinite conductivity to signal incomplete filling of the tube bore 22. In another apparatus and process illustrated in FIG. 4, a coil 38 is placed at the tube tip 20. The coil 38 can be part of a resonant circuit 40 that counts pulses as particles pass through the coil field at tip 20.

Plugging of the flow path of particles 12 into bore 22 can be detected with a pressure sensor 42 (FIG. 1) that signals maximum vacuum capability. The sensor 42 can comprise a membrane switch or a particle stop with upper sensor inserted into tube body 18. When the tip 20 of the tube body 18 is plugged by oversize particles, pressure decreases. It is known that the bore is plugged when a vacuum is sensed at a level below a limit established for a particle-filled tube bore 22. Then the device can be signaled to reverse flow, to unclog and to reinitiate sampling. Complete dispensing of particles 12 can be sensed by the same pressure monitor used to sense clogs.

Examples of particles that are the subject of the invention include ion exchange resin particles having a wide range of functionalities such as acid functionality, base functionality, chelating functionality, etc. The particles can have functionality for attachment of other reactants. Or the particles can have oxidizing or reducing capability. For example, the particles can be polystyrenes with hydride functionalities or metal complexes in high oxidative states. The particles can be organic or inorganic. Ceramic, glass and metal particles are examples. The particles can be catalysts or catalyst supports. The apparatus and process can be used to transfer ion exchange resin particles that are used as catalysts in certain organic reactions. The invention is particularly useful in combinatorial chemistry to provide automated counting and dispensing of beads.

The following example is provided in order that those skilled in the art will be better able to understand and practice the present invention. This example is intended to serve as an illustration and not as a limitation of the present invention as defined in the claims herein.

EXAMPLE

A device was constructed in accordance with FIG. 1. A three-way Luer-lock valve was attached to a 32 mm length of Teflon® tubing (1.7 mm outside diameter (OD) and 1.06 mm inside diameter (ID)) and a gas tight syringe was attached to one of the free ports of the valve. A bent wire was inserted into the tubing to define an inside tube length to act as a stop. The tip of the measuring tube was immersed into a stirred water slurry of ion-exchange resin particles that had an average (wet) diameter of 0.7 mm as measured by image analysis of a light microscopy image. The syringe plunger was withdrawn to generate a vacuum in the measuring tube to cause the slurry to enter the tube until the particles filled the tube from the open end to the stop. Movement of the syringe plunger was stopped and flow of liquid ceased. No particles adhered to the tip or outside of the measuring tube. The device was then transported to a 1.8 ml gas chromatography glass shell vial simulating a well in a reactor array. The device was positioned above the vial and the syringe plunger depressed causing a reverse flow of liquid that expelled all particles into the vial. This procedure was repeated 17 times and the number of particles transported each time was 32±1. The distribution consisted of 1 set of 31, 12 sets of 32 and 4 sets of 33 particles. Several of the 33 particle sets contained one broken particle.

Figure 5:
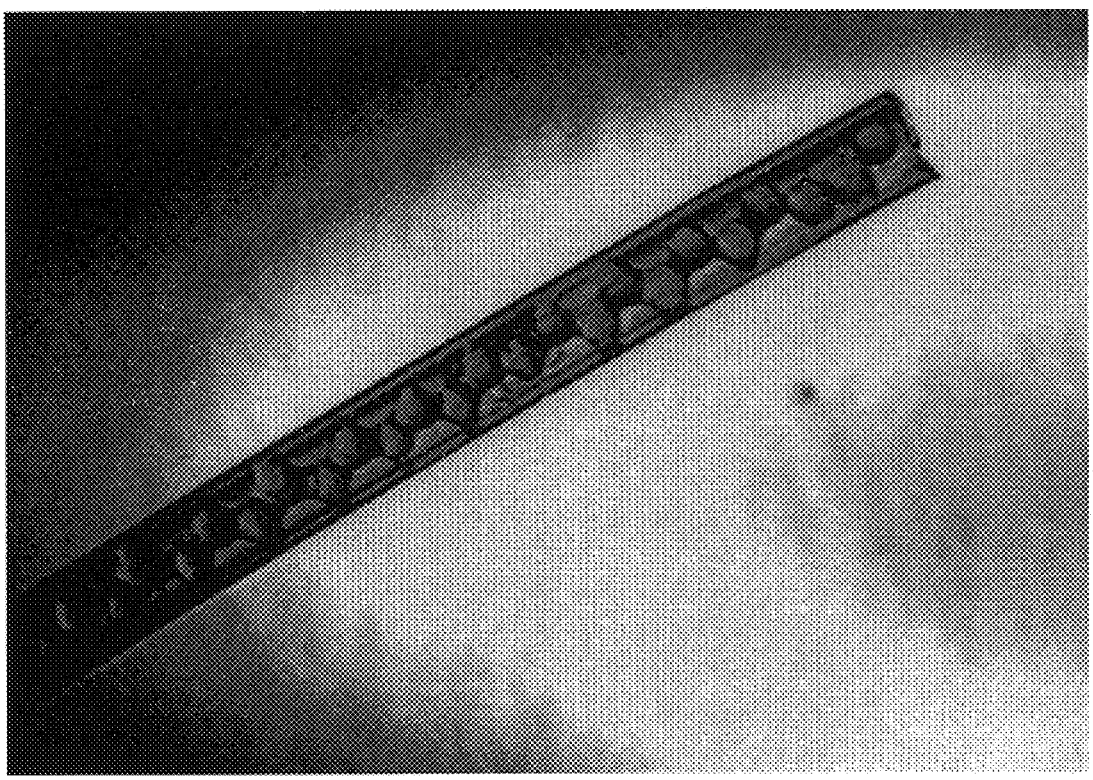
FIGS. 5 to 7 are photographs of tubular bodies of the apparatus.
Figure 6:
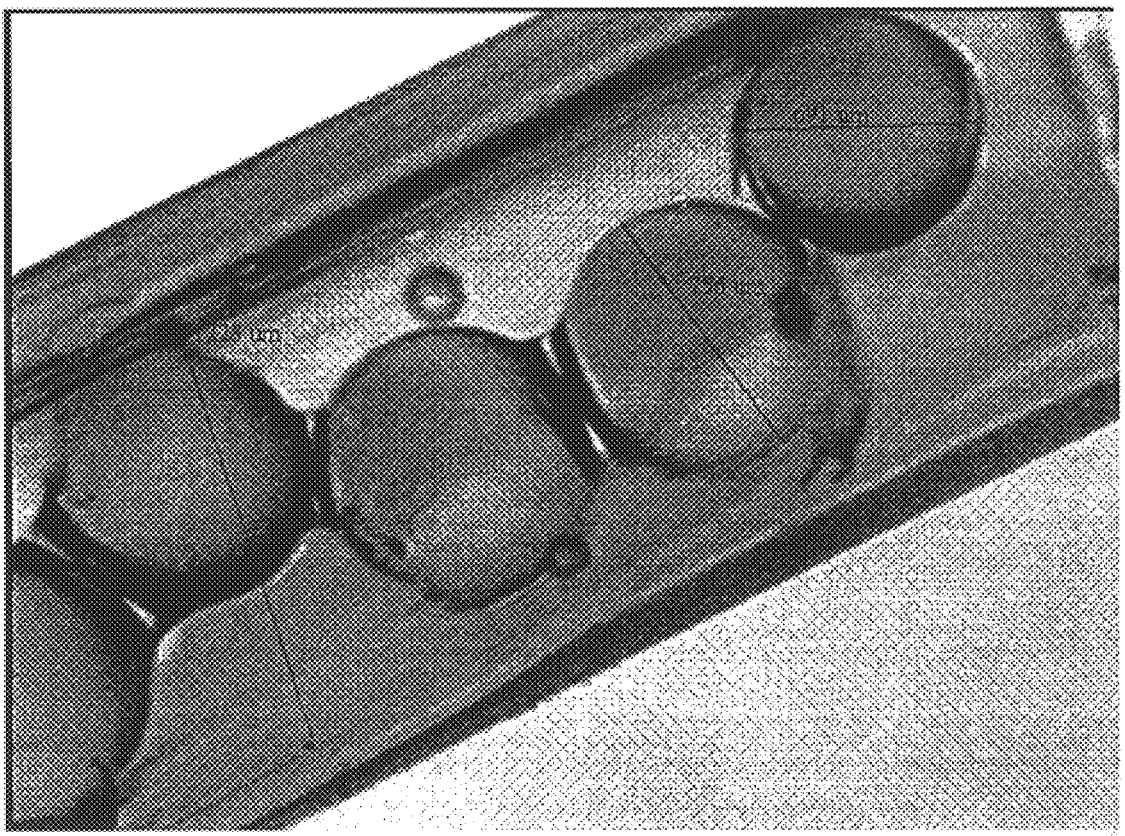
Figure 7:
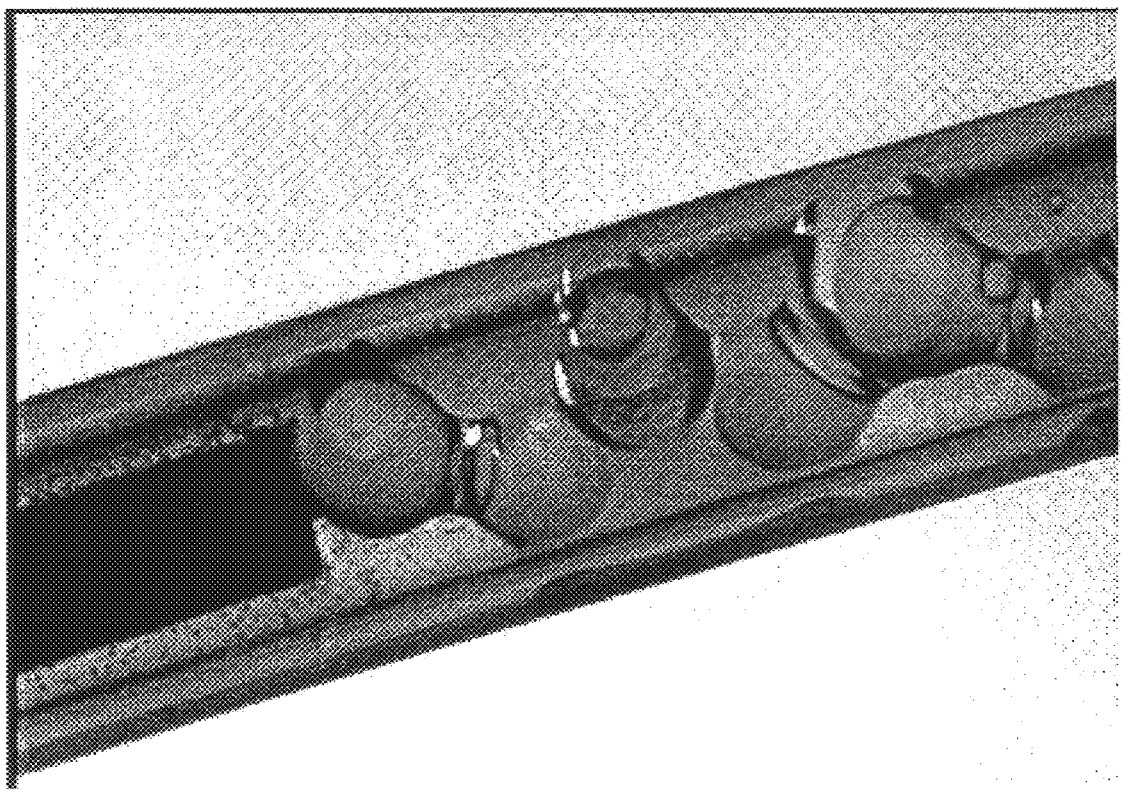

A photograph of the test apparatus showing particles contained in the Teflon® tube is shown in FIG. 5. A close-up of particles near the open end of the tube is shown in FIG. 6. The FIG. 6 test run tube was characterized by a bore to particle diameter ratio of 1.5 to 1. The two center particles in the image in FIG. 6 show stacking. FIG. 7 shows beads abutting obstruction 30.

The Example establishes that the apparatus and process of the invention can be used to accurately select, transport and position small particles.

It will be understood that each of the elements described above, or two or more together, may also find utility in applications differing from the types described herein. While the invention has been illustrated and described as embodied in an apparatus and process for selecting and positioning particles, it is not intended to be limited to the details shown, since various modifications and substitutions can be made without departing in any way from the spirit of the present invention. For example, various analytical techniques can be used in concert with the present apparatus and process when needed. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. An apparatus for selecting and positioning particles, comprising:
    a hollow tubular body containing said particles, (a) the body being of a cross-section size larger than the diameter of any single particle of said particles but smaller than twice said diameter to accommodate passage of a single particle of said particles at a time through said hollow tubular body and (b) of a length to accommodate a predetermined number of particles;
    an obstruction within said body that permits passage of fluid but prevents passage of a particle of said particles; and
    a force applicator at one end of said tubular body to apply a force to draw a flow of fluid into an end of said tubular body to fill said hollow tubular body with particles along a length of said tubular body up to said obstruction and to maintain said force so as to retain said particles within said body while transporting said retained particles to a location.

2. The apparatus of claim 1, further comprising electrical leads applied at opposite ends of said body, said leads being connected to a sensor to sense continuity of contact of particles retained within said body.

3. The apparatus of claim 1, further comprising a resonant circuit including a coil located at a tip of said tubular body to sense pulses as particles pass through a coil field generated by said coil.

4. The apparatus of claim 1, comprising a tubular body having a bore with a diameter ratio to particle diameter of less than 2 to 1.

5. The apparatus of claim 1, comprising a tubular body having a bore with a diameter ratio to particle diameter of less than 1.5 to 1.

6. A process for selecting and positioning particles, comprising:
    applying a force to draw a flow of fluid with suspended particles into an end of a hollow tubular body and through said body;
    impeding said flow in a manner so as to permit fluid to continue to flow while retaining particles within said body at a predetermined point so as to load said body with a selection of particles; and
    positioning a particle of said selection into each well of a two-dimensional array of wells for charging to a combinatorial organic synthesis reaction.

7. The process of claim 6, wherein positioning said particle comprises transporting said selection of particles to said array of wells and reversing the applying of said force to reverse fluid flow so as to discharge said particle of said selection into each well of said array.

8. A process for selecting and positioning particles, comprising:
    establishing a suspension comprising a mixture of substantially uniform sized particles in a fluid;
    introducing a hollow tubular element into said suspension, said element comprising (i) a hollow tubular body (a) of a cross-section size larger than the diameter of any single particle of said particles but smaller than twice said diameter to accommodate passage of a single particle of said particles at a time through said hollow tubular body and (b) of a length to accommodate a predetermined number of particles and (ii) an obstruction within said body that permits passage of fluid but prevents passage of a particle of said particles;
    applying a force to draw a flow of fluid and particles into an end of said element to fill said hollow tubular body with particles from said particles along a length of said body up to said obstruction; and
    maintaining said force so as to retain said particles within said body while transporting said retained particles to a location; and
    depositing said retained particles at said location by releasing said force.

9. The process of claim 8, further comprising applying an electrical lead to opposite end particles of said retained particles within said tubular body to sense whether the particles are in continuous contact to determine complete filling of the tubular body with retained particles.

10. The process of claim 8, further comprising counting particles passing by a tip of the tubular body as particles are drawn into said body to determine complete filling of the tubular body with retained particles.

11. The process of claim 8, further comprising monitoring pressure of said force.

12. The process of claim 8, further comprising detecting pressure within said tubular body.

13. The process of claim 8, further comprising detecting pressure within said tubular body and comparing said pressure to a threshold pressure to determine clogging of said tubular body.

14. The process of claim 8, further comprising detecting pressure within said tubular body, comparing said pressure to a threshold pressure to determine clogging of said tubular body and reversing fluid flow into said body when said body is clogged and then reapplying said force to draw a flow of fluid into said end of said element.

15. The process of claim 8, further comprising detecting pressure within said tubular body to determine discharge of particles from said body.

16. The process of claim 8, wherein the particles have an acid functionality, base functionality or chelating functionality.

17. The process of claim 8, wherein the particles have a functionality for attachment of other reactants.

18. The process of claim 8, wherein the particles have oxidizing or reducing capability.

19. The process of claim 8, wherein the particles are organic or inorganic.

20. The process of claim 8, wherein the particles are ceramic, glass or metal.

21. The process of claim 8, wherein the particles are ion exchange resin particles.

22. The process of claim 8, wherein the particles are beads used in combinatorial chemical synthesis.

* * * * *